US00PP16333P3

(12) United States Plant Patent
Lyrene

(10) Patent No.: US PP16,333 P3
(45) Date of Patent: Mar. 14, 2006

(54) BLUEBERRY PLANT CALLED 'SPRINGWIDE'

(50) Latin Name: *Vaccinium corymbosum*
Varietal Denomination: Springwide

(75) Inventor: Paul M. Lyrene, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 172 days.

(21) Appl. No.: 10/871,998

(22) Filed: Jun. 21, 2004

(65) Prior Publication Data

US 2005/0283864 P1 Dec. 22, 2005

(51) Int. Cl.
*A01H 5/00* (2006.01)

(52) U.S. Cl. ..... Plt./157

(58) Field of Classification Search ..... Plt./157
See application file for complete search history.

*Primary Examiner*—Anne Marie Grunberg
*Assistant Examiner*—Annette H Para

(57) ABSTRACT

A new and distinct low-chill blueberry (*Vaccinium corymbosum*) cultivar. Its novelty lies in the following unique combination of features:

1. Has a very low chilling requirement of about 200 hours below 7° C.
2. Produces a large berry with medium blue color and good scar, firmness, and flavor.
3. Ripens early, with first commercial harvest about April 5 at Sebring Fla. and April 15 at Windsor, Fla.
4. Has a bush of medium vigor that is midway between spreading and upright.

4 Drawing Sheets

Latin name of the genus and species: *Vaccinium corymbosum* L.
Variety denomination: 'Springwide'.

BACKGROUND OF THE INVENTION

Southern highbush blueberries are grown in areas where winters are too mild to permit cultivation of northern highbush blueberry cultivars, all of which have a high chilling requirement. As one moves farther and farther south down the Florida peninsula and to areas with warmer and warmer winters in other parts of the world, the harvest season becomes earlier and earlier, but varieties with lower and lower chilling requirements are needed for commercial production. Adaptation to areas with mild winters requires that both flower buds and leaf buds sprout vigorously in the spring after having received only a short period of winter chilling.

The University of Florida has been breeding to develop low-chill highbush blueberry varieties since 1950. Recurrent selection is being used to improve the adaptation of the plants, the yields, and the quality of the berries. 'Springwide' was selected from the cross FL83-132 (unpatented)× 'Sharpblue' (unpatented) which was made in a greenhouse in Gainesville, Fla. in 1984. The seedling was first fruited in a field evaluation nursery in Gainesville in the spring of 1986. The plant was asexually propagated by softwood cuttings to plant 10-plant plots in Gainesville, Sebring, and Windsor between 1990 and 1994. In January 1998, 10-plant plots propagated from softwood cuttings were planted at 5 other locations in Florida. In all cases, plants from softwood cuttings have been uniform and have not shown deviations from the variety characteristics. 'Springwide' has been outstanding in its ability to leaf and flower well and ripen early in the season in the low-chill production areas in the central Florida peninsula.

BRIEF SUMMARY OF THE INVENTION

'Springwide' is a new southern highbush blueberry variety that has the following unique combination of characteristics that set it apart from other blueberry cultivars.

a. Has a low chilling requirement. Both leaf and flower buds break dormancy in the early spring, even in areas receiving as little as 200 hours per winter with temperatures below 7° C.

b. Produces berries that are large, firm, medium blue in color, and have a small, dry picking scar.

c. Ripens most of its berries between April 5 and May 1 in Sebring, Fla. and between April 15 and May 10 in Windsor, Fla. At Windsor, it averages ripening about 5 days earlier than 'Star' (U.S. Plant Pat. No. 10,675), 'Emerald' (U.S. Plant Pat. No. 12,165), and 'Jewel' (U.S. Plant Pat. No. 11,807).

d. Produces a semi-erect bush with medium vigor and good ability to persist in the field.

e. 'Springwide' differs from its parents in many details, as would be expected for a seedling from a cross between two highly-heterozygous clones. Compared to parent FL83-132, 'Springwide' flowers much earlier in the spring (reflecting a lower chilling requirement), ripens earlier in the season, and produces a berry that is lighter blue in color. The berry of FL83-132 is quite dark. Compared to the other parent, 'Sharpblue', 'Springwide' ripens a week earlier and produces a berry with a much better (smaller, drier) picking scar. In addition, berry size does not decline precipitously between the first and last picking of the season on 'Springwide' as it does with 'Sharpblue'.

BRIEF DESCRIPTION OF THE DRAWING

The color chart used in this specification is "The Pantone Book of Color", by Leatrice Eiseman and Lawrence Herbert.

1990. Harry N. Abrams, Inc., Publishers, N.Y. Where colors in the drawings differ from the Pantone color designations in the verbal descriptions, the Pantone color designations are the more accurate.

DETAILED BOTANICAL DESCRIPTION

Figure 1:
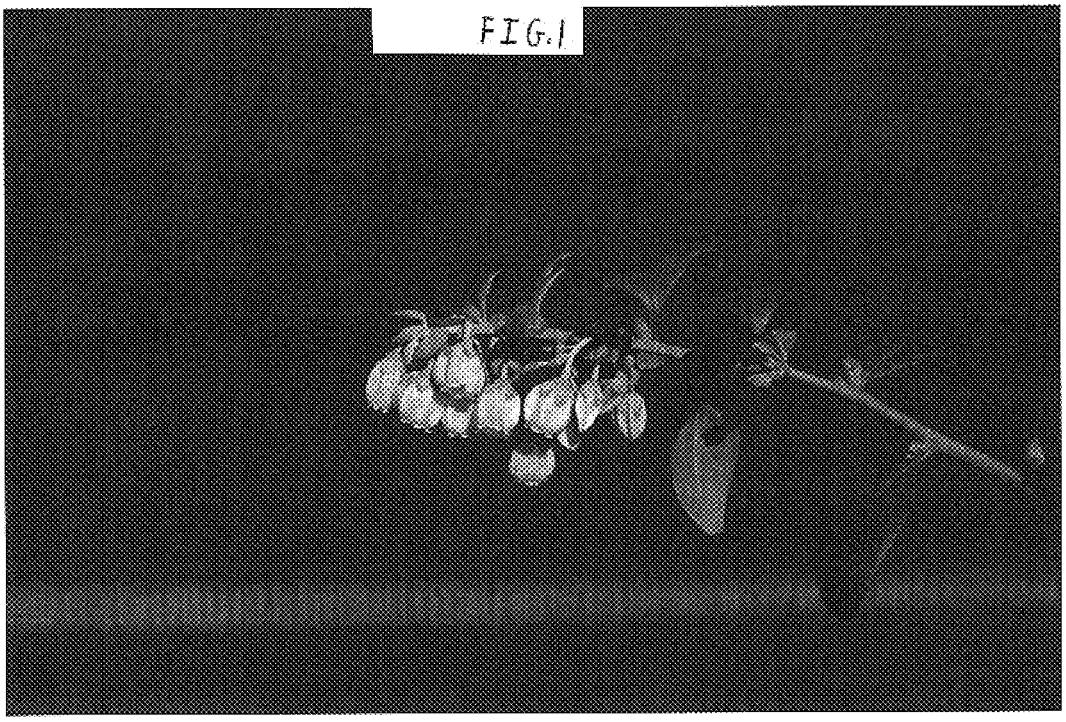
FIG. 1 shows flower clusters of 'Springwide' during February on young plants that were maintained evergreen in a greenhouse. This environment elongates the peduncles compared to what would be seen on field-grown plants that have been chilled before flowering. The white corollas and urceolate flowers are typical.
Figure 2:
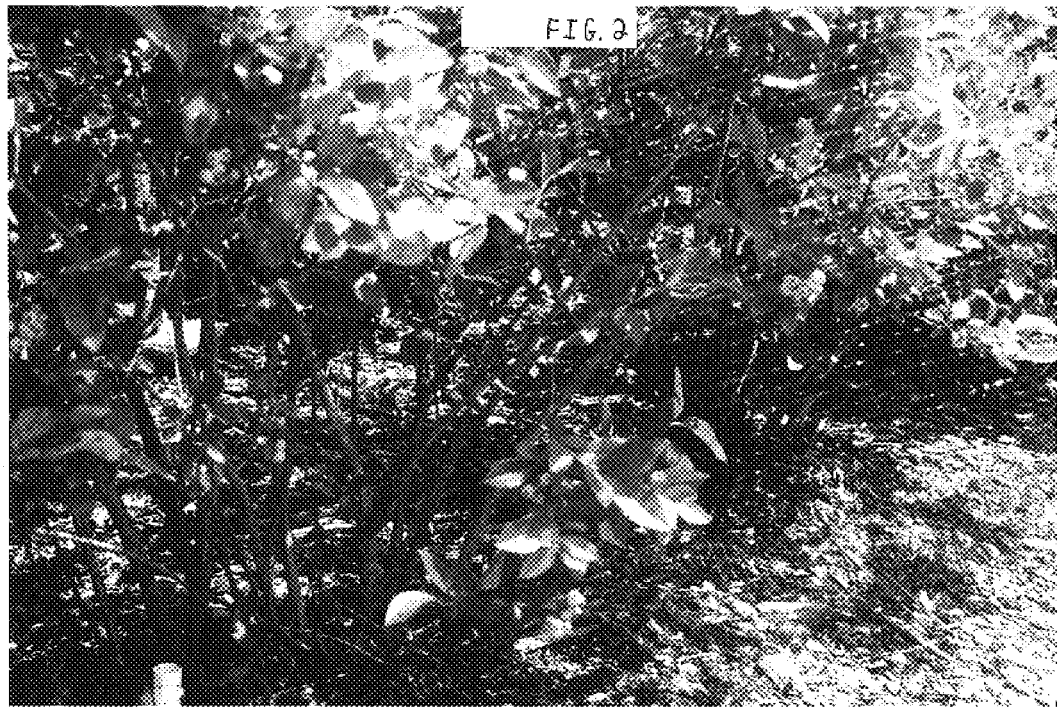
FIG. 2 shows the lower parts of two 5-year-old plants in the field in early May. The tendency to make multiple canes from the base, giving the plant a somewhat spreading habit, can be seen.
Figure 3:
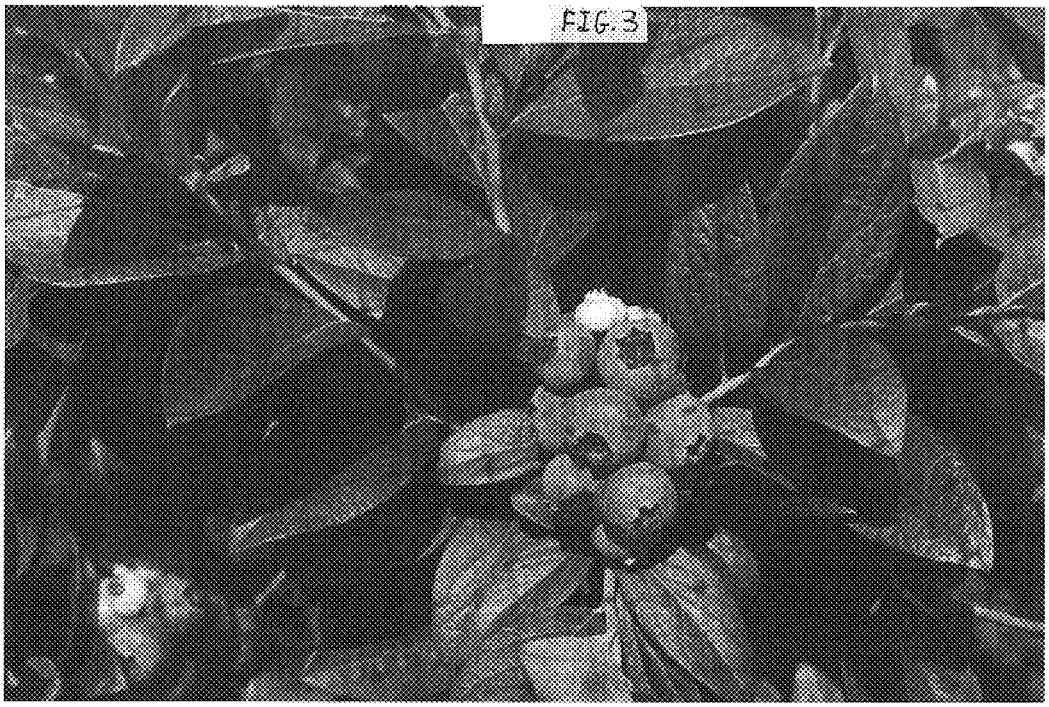
FIG. 3 shows at close range a cluster of berries in late April on a field-grown plant. The dark green leaves and frosty-blue berries are typical.
Figure 4:
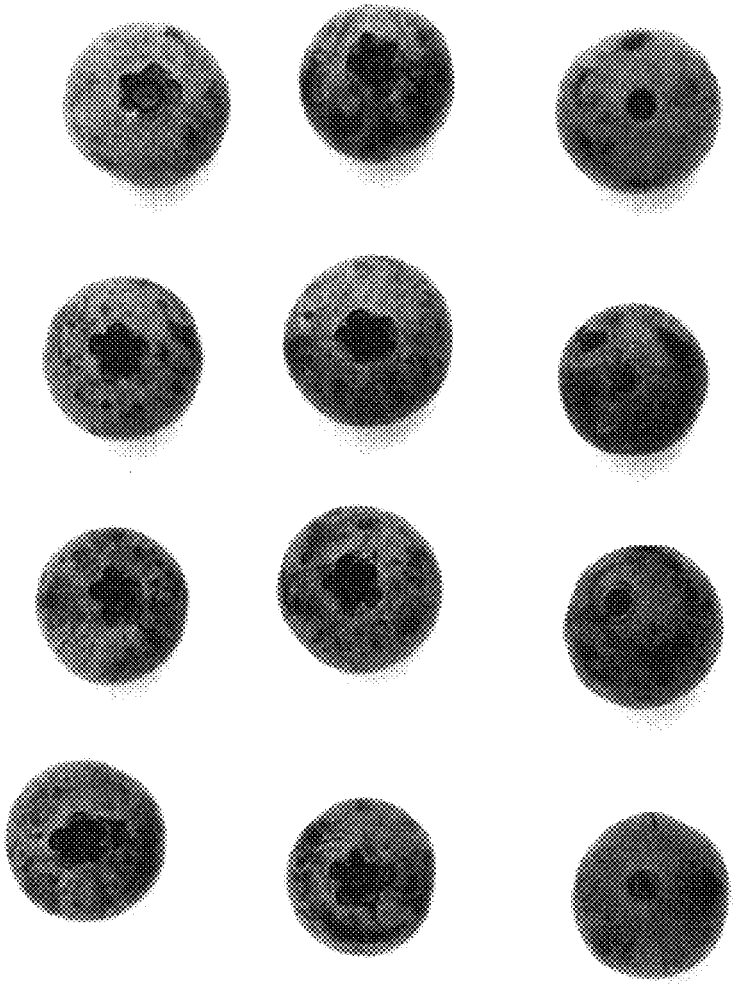
FIG. 4 shows, at close range, the mature berries. The small picking scar can be seen in the column on the right and the flat, slightly-developed calyx lobes can be seen in the two columns on the left.

Market class: 'Springwide' produces southern highbush blueberries suitable for both the fresh and frozen market.

Bush: Plant characteristics were measured on 6-year-old plants growing in a commercial blueberry field at Windsor, Fla. The plants were irrigated, pruned, and fertilized according to commercial practices on blueberry farms in that area.

- *Plant height.*—1.5 m.
- *Canopy diameter measured at the widest part of the bush.*—1.3 cm.
- *Plant vigor.*—Medium.
- *Growth habit.*—Between erect and spreading. Has 10 to 15 major canes arising from a base 40 cm across.
- *Flower bud density (number) along flowering twigs in January.*—Medium.
- *Twigginess.*—Low to medium.
- *Tendency to remain evergreen in winter.*—Medium to low.

Trunk and branches:

- *Suckering tendency.*—Medium. On 6-year-old plants, ten to 15 main canes arising from a base 40 cm across.
- *Surface texture of strong, 6-month-old stems observed August 18.*—Smooth.
- *Surface texture of strong, 1-year-old stems observed August 18.*—Smooth but becoming rough due to formation of vertical fissures through which rough bark emerges.
- *Surface texture of 3-year-old canes.*—Rough, with vertically oriented rectangles of exfoliating bark.
- *Surface color of 6-month-old strong shoots observed August 18.*—'Buckskin' (Pantone 16-1342).
- *Surface color of surface of 1-year-old rough bark observed August 18.*—'Baked clay' (Pantone 18-1441).
- *Surface color of 3-year-old rough-textured canes.*—'Pebble' (Pantone 14-1112).
- *Internode length on strong, upright shoots measured August 18.*—1.9 cm.

Leaves:

- *Leaf length including petiole, from tip of petiole to end of blade.*—Mean 68 mm.
- *Leaf width at widest point.*—36 mm.
- *Leaf shape.*—Oval. Midrib terminates in a dew tip, which is about 0.5 mm long and is visible at 15× magnification.
- *Leaf margin.*—Entire.
- *Color of upper surface of leaves.*—'Cedar' (Pantone 16-0526).
- *Color of lower surface of leaves.*—'Willow green' (Pantone 15-0525).
- *Pubescence on upper surface of leaf.*—None.
- *Pubescence on lower surface of leaf.*—None.
- *Pubescence on leaf margin.*—None.
- *Relative time of leafing and flowering.*—Tends to flower about a week before the leaf buds sprout in the spring.

Flowers:

- *Flower arrangement.*—Flowers arranged alternately along a short, leafless, deciduous branch.
- *Flower fragrance.*—Distinct honeysuckle fragrance if newly opened flowers are harvested and stored in a closed container for 15 minutes.
- *Pedicel length at time of anthesis.*—5 mm.
- *Peduncle length at time of anthesis.*—Variable; averages about 8 mm.
- *Petals.*—Fused into a corolla tube with 5 lobes.
- *Pollen staining.*—Approximately 99% of the pollen grains stain with acetocarmine dye, indicating that a high percentage of the pollen grains are well-formed, starch-filled, and potentially viable.
- *Pollen abundance.*—Dried flowers shed pollen in great abundance.
- *Pollen color.*—'Straw'. Pantone 13-0922.
- *Flower type.*—Perfect, ovary inferior, petals fused into a corolla tube, the 10 stamens inserted at the base of the corolla tube.
- *Flower length from pedicel attachment point to corolla tip.*—11 mm.
- *Length of corolla tube.*—9.5 mm.
- *Style length from top of ovary to stigma tip.*—9 mm.
- *Calyx diameter at anthesis from tip of one lobe to tip of the opposite lobe.*—7 mm.
- *Diameter of corolla tube at widest point.*—8 mm.
- *Corolla aperture diameter.*—3.5 mm.
- *Corolla surface texture.*—Smooth.
- *Flower shape.*—Urceolate.
- *Corolla color at anthesis.*—White — the color of the unprinted spaces in the Pantone Book of Color.
- *Style color at anthesis.*—'Green banana', Pantone 14-0434.
- *Pedicel and peduncle color.*—'Apple green', Pantone 15-0543.
- *Flowering period.*—Average date when first 50% of the flowers open at Gainesville, Fla. is February 22. This compares with the following dates for some other varieties: Emerald (U.S. Plant Pat. No. 12,165): February 20; 'Jewel' (U.S. Plant Pat. No. 11,807): February 20; Millennia (U.S. Plant Pat. No. 12,816): February 19; Star (U.S. Plant Pat. No. 10,675): March 2.
- *Flower cluster (tight, medium, or open).*—Medium.
- *Average number of flowers per cluster.*—7.
- *Location of tip of stigma relative to the lip of the corolla.*—Tip of style extends to a position slightly (less than 1 mm) beyond the longest corolla lobes.
- *Distance between the stigma tip and the part of the anther pore nearest the stigma tip.*—2.5 mm.

Berry:

*Mean date of first commercial harvest (25% fruit ripe) at Windsor, Fla.*—April 22.

*Mean date of last commercial harvest at Windsor, Fla.*—May 15.

*Diameter of calyx aperture on mature berry.*—7.4 mm.

*Calyx lobes on mature berry.*—Small and puckered outward.

*Berry cluster (tight, medium, or loose).*—Medium to tight.

*Pedicel length on ripe berry.*—Mean 7.5 mm.

*Peduncle length on fruit clusters at the time of fruit ripening.*—Highly variable. Mean 12 mm.

*Number of berries per cluster.*—Mean 6.1; mostly 5 to 7.

*Detachment force required to pick ripe berry (low, medium, or high).*—Medium to high.

*Mean berry weight.*—3.1 g per berry for first half of harvest on well-pruned bushes.

*Mean berry height.*—13.1 mm.

*Mean berry width.*—19.3 mm.

*Surface color of mature berry on the plant.*—'Storm gray' (Pantone 15-4003).

*Surface color of mature berry after harvest and packing.*—'Gull' (Pantone 17-3802).

*Surface color of mature berry after polishing.*—'Shale' (Pantone 19-3903).

*Berry surface wax.*—Medium to high in quantity; Medium to high in persistence.

*Mature berry internal flesh color.*—'Willow green' (Pantone 15-0525).

*Pedicel scar on the berry.*—Small and dry.

*Berry firmness.*—High.

*Berry flavor.*—Very sweet and slightly acid.

*Berry texture.*—Good. Small seeds and thin skins.

*Color of dried seeds.*—'Brown sugar' (Pantone 17-1134).

*Mean weight of dried, well-developed seeds.*—0.39 mg.

*Mean length of well-developed seeds.*—1.5 mm.

*Mean width of well-developed seeds.*—0.8 mm.

Physiological characteristics:

*Chilling requirement.*—200 hours per winter below 7° C.

*Cold hardiness.*—Flowers and fruit hardy to −3° C. The plant, during winter dormancy, is hardy to −15° C.

*Productivity.*—Medium. Plants average about 4 pounds when 4-years-old in north Florida.

*Ease of propagation.*—Propagates readily from softwood cuttings under mist. Several hundred plants have been propagated at Gainesville, Fla., and all have the characteristics of the variety.

Diseases, insects, mites:

*Phytophthora root rot.*—Appears to be above average in resistance.

*Stem blight (Botryosphaeria dothidia).*—Appears to have good resistance.

*Cane canker (Botryosphaeria corticis).*—Appears to be resistant to the common races in north Florida.

*Fungal leaf spots (many fungal pathogens).*—Has average resistance. Fungicidal sprays during the growing season after harvest will be needed to maximize yields in warm, humid environments.

*Overall survival in the field.*—Good. Survival appears to equal or surpass that of most other southern highbush blueberry varieties.

It is claimed:

1. A new and distinct southern highbush blueberry plant, substantially as illustrated and described, characterized by having a durable, low-chill bush that produces large, high-quality berries that ripen in late April and early May in northeast Florida.

* * * * *